US00PP26245P2

(12) United States Plant Patent
Hooijman

(10) Patent No.: US PP26,245 P2
(45) Date of Patent: Dec. 22, 2015

(54) ROSE PLANT NAMED 'ESM R073'

(50) Latin Name: *Rosa hybrida*
Varietal Denomination: ESM R073

(71) Applicant: Aloysius A. J. Hooijman, Aalsmeer (NL)

(72) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 120 days.

(21) Appl. No.: 13/987,855

(22) Filed: Sep. 9, 2013

(51) Int. Cl.
*A01H 5/02* (2006.01)

(52) U.S. Cl.
USPC ..... Plt./146

(58) Field of Classification Search
USPC ..... Plt./146
See application file for complete search history.

(56) References Cited

PUBLICATIONS

UPOV hit on Rose plant named 'ESM R073', www.upov.int, QZ PBR 20112029, filed Aug. 25, 2011 and published Oct. 15, 2011.*
Plant Breeders' Rights application QZ PBR *Rosa* 'ESM R073', published Oct. 15, 2015.*
PVP Detail for Rose 'ESM R073' published Oct. 15, 2015.*

* cited by examiner

*Primary Examiner* — Anne Grunberg
(74) *Attorney, Agent, or Firm* — C. A. Whealy

(57) ABSTRACT

A new and distinct cultivar of Rose plant named 'ESM R073', characterized by its upright and strong flowering stems; vigorous growth habit and high productivity; freely flowering habit; orange-colored flowers that are typically grown as spray types; excellent postproduction longevity; and resistance to *Botrytis*.

1 Drawing Sheet

Botanical designation: *Rosa hybrida*.
Cultivar denomination: 'ESM R073'.

CROSS-REFERENCED TO CLOSELY-RELATED APPLICATIONS

Applicant: Aloysius A. J. Hooijman
Title: Rose Plant Named 'ESM R071'
Filed: Sep. 9, 2015
Application Number: U.S. Plant patent application Ser. No. 13/987,858

BACKGROUND OF THE INVENTION

The present Invention relates to a new and distinct cultivar of Rose plant, botanically known as *Rosa hybrida*, commercially used as a cut flower Rose plant, typically referred to as a floribunda type, and hereinafter referred to by the name 'ESM R073'.

The new Rose plant is a product of a planned breeding program conducted by the Inventor in El Quinche, Pichincha, Ecuador. The objective of the breeding program was to develop new cut flower Rose varieties with attractive flowers and excellent postproduction longevity.

The new Rose plant originated from a cross-pollination made by the Inventor in July, 2007 of a proprietary Rose selection identified as Line 369, not patented, as the female, or seed, parent with a proprietary Rose selection identified as Line 222, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in March, 2009.

Asexual reproduction of the new Rose plant by bud grafting in El Quinche, Pichincha, Ecuador since October, 2009 has shown that the unique features of this new Rose plant are stable and reproduced true to type in successive generations of asexual reproduction.

SUMMARY OF THE INVENTION

Plants of the new Rose have not been observed under all possible environmental conditions and cultural practices. The phenotype may vary somewhat with variations in environmental conditions such as temperature and light intensity, without however, any variance in genotype.

The following traits have been repeatedly observed and are determined to be the unique characteristics of 'ESM R073'. These characteristics in combination distinguish 'ESM R073' as a new and distinct Rose plant:

1. Upright and strong flowering stems.
2. Vigorous growth habit and high productivity.
3. Freely flowering habit.
4. Orange-colored flowers that are typically grown as spray types.
5. Excellent postproduction longevity.
6. Resistant to *Botrytis*.

Plants of the new Rose differ from plants of the female parent selection in the following characteristics:

1. Plants of the new Rose are taller than plants of female parent selection.
2. Stems of plants of the new Rose have slightly more thorns than stems of plants of the female parent selection.

3. Plants of the new Rose and the female parent selection differ in flower color as plants of the female parent selection have light red-colored flowers.

Plants of the new Rose differ from plants of the male parent selection in the following characteristics:

1. Plants of the new Rose are slightly shorter than plants of the male parent selection.
2. Plants of the new Rose are more vigorous than plants of the male parent selection.
3. Stems of plants of the new Rose have slightly more thorns than stems of plants of the male parent selection.
4. Flowers of plants of the new Rose have more petals than flowers of plants of the male parent selection.
5. Flower buds and flowers of plants of the new Rose are larger than flower buds and flowers of plants of the male parent selection.

Plants of the new Rose can be compared to plants of Rose 'Babe', not patented. In side-by-side comparisons conducted in El Quinche, Pichincha, Ecuador, plants of the new Rose differed from plants of 'Babe' in the following characteristics:

1. Plants of the new Rose were shorter and broader than plants of 'Babe'.
2. Plants of the new Rose were more vigorous than plants of 'Babe'.
3. Plants of the new Rose had stronger stems than plants of 'Babe'.
4. Stems of plants of the new Rose had more thorns than stems of plants of 'Babe'.
5. Plants of the new Rose had taller and broader flower sprays than plants of 'Babe' with more flowers per spray.
6. Plants of the new Rose flower about 13 days later than plants of 'Babe'.
7. Plants of the new Rose had larger flower buds and flowers than plants of 'Babe'.
8. Flowers of plants of the new Rose had more petals than flowers of plants of 'Babe'.

Plants of the new Rose can also be compared to plants of *Rosa hybrida* 'ESM R071', disclosed in U.S. Plant patent application Ser. No. 13/987,858, primarily in flower color as plants of 'ESM R071' have dark yellow-colored flowers.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph at the upper left of the sheet comprises a side perspective view of typical flowering stem of 'ESM R073'.

The photograph at the upper right of the sheet is a close-up view of a typical flowering stem of 'ESM R073'.

The photograph at the lower left of the sheet is a close-up view of a typical flower of 'ESM R073'.

The photograph at the lower right of the sheet are close-up views of the upper and lower surfaces of typical leaves of 'ESM R073'.

DETAILED BOTANICAL DESCRIPTION

Plants of the new Rose have not been observed under all possible environmental conditions and cultural practices. The phenotype may vary somewhat with variations in environmental conditions such as temperature and light intensity, without, however, any variance in genotype. The aforementioned photographs, following observations and measurements describe plants grown in beds in a polyethylene-covered greenhouse in El Quinche, Pichincha, Ecuador and under typical hydroponic Rose production practices. Plants were pinched 13 to 14 weeks after planting and were 79 weeks old when the description and photographs were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'ESM R073'.

Parentage:

*Female, or seed, parent.*—Proprietary seedling selection of *Rosa hybrida* identified Line 369, not patented.

*Male, or pollen, parent.*—Proprietary seedling selection of *Rosa hybrida* identified Line 222, not patented.

Propagation:

*Type.*—By bud grafting.

*Time to initiate roots.*—About seven to ten days at 26° C. to 30° C.

*Time to produce a rooted young plant.*—About four to five weeks at 22° C. to 26° C.

*Root description.*—Fibrous, medium to thick; close to N199B in color.

*Rooting habit.*—Moderately freely branching; medium density.

Plant description:

*Plant and growth habit.*—Perennial shrub; upright and strong flowering stems; typically grown as a spray-type cut flower; vigorous growth habit.

*Branching habit.*—Freely basal branching habit; highly productive with about 8.4 flowering stems developing per plant per year.

*Plant height.*—About 127 cm.

*Plant width (spread).*—About 68 cm.

*Lateral branches.*—Quantity: About 17 lateral branches develop per plant. Length: About 84 cm. Diameter: About 7 mm. Internode length: About 4.6 cm. Texture: Smooth, glabrous; older stems, woody. Color: Close to 146A. Thorns: Density: Medium. Shape: Triangular with sharp acuminate apices; slightly incurved and flat. Height: About 7 mm. Length, at base: About 8 mm. Color, immature: Close to 172A and 161A. Color, mature: Close to between 164C and 178A.

Leaf description:

*Arrangement.*—Alternate; compound with typically five to seven leaflets per leaf.

*Leaf length.*—About 17.9 cm.

*Leaf width.*—About 10.6 cm.

*Terminal leaflet length.*—About 5.8 cm.

*Terminal leaflet width.*—About 4.5 cm.

*Lateral leaflet length.*—About 5 cm.

*Lateral leaflet width.*—About 4.1 cm.

*Leaflet shape.*—Ovate.

*Leaflet apex.*—Acute.

*Leaflet base.*—Attenuate.

*Leaflet margin.*—Serrate.

*Leaflet texture, upper and lower surfaces.*—Smooth, glabrous; coriaceous.

*Leaflet venation pattern.*—Pinnate.

*Leaflet color.*—Developing leaflets, upper surface: Close to 139A; towards the margins, close to 187A. Developing leaflets, lower surface: Close to 147B. Fully expanded leaflets, upper surface: Close to 147A; venation, close to 152B. Fully expanded leaflets, lower surface: Close to 147B; venation, close to 146C.

*Petioles, leaves.*—Length: About 1.8 cm. Diameter: About 2 mm. Texture, upper surface: Prickly. Texture, lower surface: Smooth, glabrous. Color, upper and lower surfaces: Close to 146A to 146D.

*Petioles, leaflets.*—Length: About 2.6 cm. Diameter: About 1.3 mm. Texture, upper surface: Prickly. Texture, lower surface: Smooth, glabrous. Color, upper surface: Close to 146A. Color, lower surface: Close to 146A to 146C.

*Stipules.*—Arrangement and appearance: Two, adnate to the petiole, leafy in appearance. Length: About 2.4 cm. Width: About 2.1 mm. Shape: Roughly deltoid. Apex: Acuminate, tapered. Base: Tapered. Margin: Serrate. Texture, upper and lower surfaces: Irregularly pubescent; membranous. Venation pattern: Pinnate. Color, upper surface: Close to 137A. Color, lower surface: Close to 146A.

Flower description:

*Flower type and flowering habit.*—Symmetrical rosette flowers; flowers typically grown as spray types; flowers face upright.

*Flowering season.*—Plants of the new Rose flower year-round under greenhouse conditions; early flowering habit, plants begin flowering about 83 days after pinching; in the garden, optimal flowering from spring through autumn; flowering intermittent.

*Spray height.*—About 26 cm.

*Spray diameter.*—About 20 cm.

*Quantity of flowers per spray.*—About seven.

*Flower diameter.*—About 7.5 cm.

*Flower depth* (*height*).—About 3 cm.

*Flower longevity on plant.*—About 33 days; flowers persistent.

*Flower longevity as a cut flower.*—Excellent postproduction longevity, flowers last about ten to twelve days.

*Fragrance.*—Slightly fragrant, pleasant.

*Flower buds.*—Shape: Ovoid. Length: About 2.9 cm. Diameter: About 2.3 cm. Color: Close to 144A and 146A.

*Petals.*—Quantity: About 35 to 40 per flower; petals imbricate. Length: About 3.1 cm. Width: About 3.2 cm. Shape: Nearly round; transversely ovate. Apex: Blunt to shortly acute. Base: Obtuse. Margin: Entire. Texture, upper and lower surfaces: Smooth, glabrous; papery to coriaceous. Color: When opening, upper surface: Close to N30A; towards the base, close to 14A. When opening, lower surface: Close to N30C; towards the base, close to 14A. Fully opened, upper surface: Close to N30C; towards the base, close to 14A. Fully opened, lower surface: Close to N25A; towards the base, close to 13A.

*Petaloids.*—Quantity: About seven; petaloids whorled. Length: Variable. Width: Variable. Shape: Irregularly shaped. Apex: Blunt to shortly acute. Base: Obtuse. Margin: Entire or uneven. Texture, upper and lower surfaces: Smooth, glabrous; papery to coriaceous. Color: When opening and fully opened, upper surface: Close to N30A; towards the base, close to 13A. When opening and fully opened, lower surface: Close to 32A; towards the base, close to 14A.

*Sepals.*—Quantity per flower: Typically five in a single whorl. Length: About 3 cm. Width: About 1 cm. Shape: Roughly deltoid. Apex: Tapered. Base: Truncate. Margin: Entire; glandular. Texture, upper surface: Pubescent; leathery. Texture, lower surface: Glandular; along the margins, irregularly pubescent; leathery. Color: When opening, upper surface: Close to 146B to 146D. When opening, lower surface: Central spot, close to 175A; towards the margins, close to 144A and 146A; towards the base, close to 144B. Fully opened, upper surface: Close to 145B and 146B. Fully opened, lower surface: Close to 144B and 146B.

*Pedicels.*—Length: About 3.1 cm. Diameter: About 3.2 mm. Strength: Strong. Aspect: About 34° from vertical. Texture: Glandular. Color: Close to 146A and N199D.

*Reproductive organs.*—Stamens: Quantity: About 100 per flower. Anther length: About 2.5 mm. Anther shape: Reniform. Anther color: Close to 162A and N163D. Filament color: Close to 160C and 46B. Pollen amount: Abundant. Pollen color: Close to 163A.

*Pistils.*—Quantity: About 109 per flower. Pistil length: About 1.2 cm. Stigma shape: Broadly reniform. Stigma color: Close to 153B. Style length: About 8.4 mm. Style color: Close to 17A. Receptacle height: About 8 mm. Receptacle diameter: About 9 mm. Receptacle shape: Cup-shaped. Receptacle texture: Smooth, glabrous. Receptacle color: Close to 144A.

*Fruits.*—Length: About 1.8 cm. Diameter: About 2 cm. Texture: Smooth. Color: Close to N172A.

*Seeds.*—Quantity per fruit: About six. Length: About 6 mm. Diameter: About 5 mm. Texture: Smooth. Color: Close to 160B.

Pathogen & pest tolerance/resistance: Plants of the new Rose have been observed to resistant to *Botrytis*. Plants of the new Rose have not been observed to be resistant or tolerant to pests and other pathogens.

Temperature tolerance: Plants of the new Rose have been observed to tolerate temperatures ranging from 0° C. to 35° C.

It is claimed:

1. A new and distinct Rose plant named 'ESM R073' as illustrated and described.

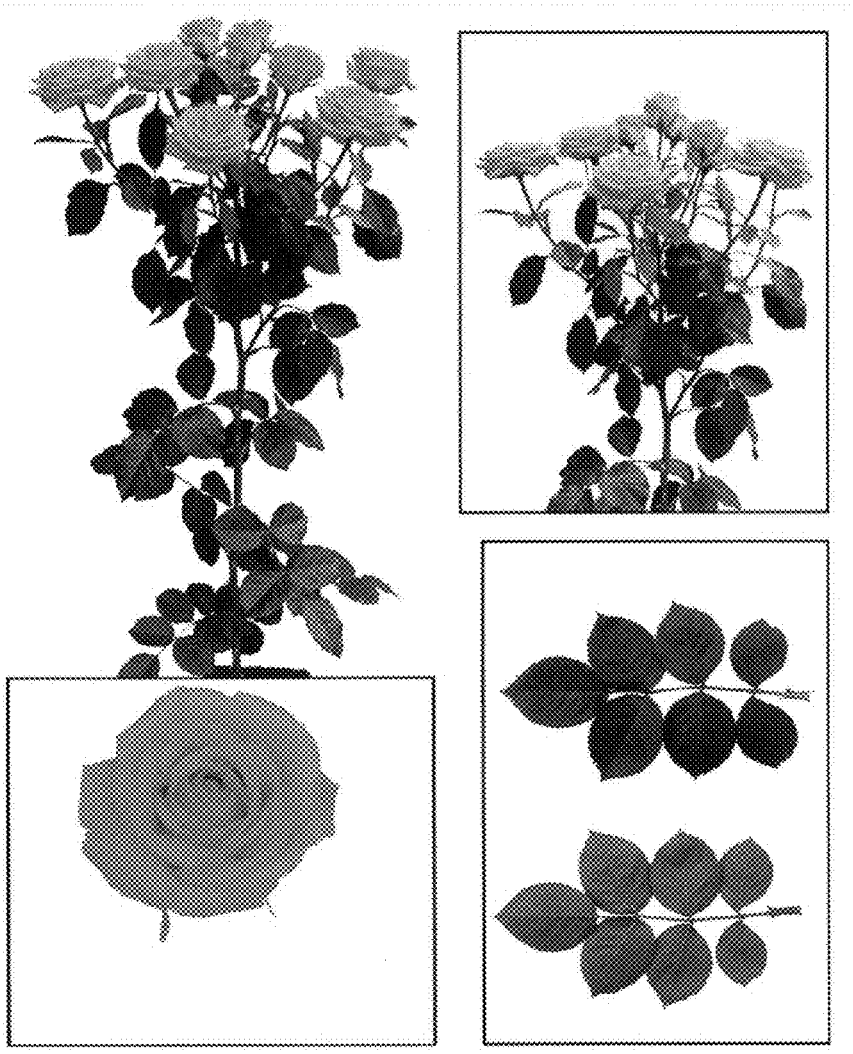

* * * * *